United States Patent [19]

Martens

[11] Patent Number: 4,720,702
[45] Date of Patent: Jan. 19, 1988

[54] METHOD AND APPARATUS FOR MONITORING THE TENSION OF AN ADVANCING YARN

[75] Inventor: Gerhard Martens, Remscheid, Fed. Rep. of Germany

[73] Assignee: Barmag AG, Remscheid, Fed. Rep. of Germany

[21] Appl. No.: 881,124

[22] Filed: Jul. 2, 1986

[30] Foreign Application Priority Data

Jul. 3, 1985 [DE] Fed. Rep. of Germany ....... 3523710

[51] Int. Cl.$^4$ ............................................. G08B 21/00
[52] U.S. Cl. .................................... 340/677; 28/187; 57/81; 66/163
[58] Field of Search ............................ 340/677; 66/163; 19/0.2, 0.22; 28/187; 57/81, 264, 265

[56] References Cited

U.S. PATENT DOCUMENTS 3,731,069  5/1973  Goto et al. ........................... 340/677
4,178,590 12/1979  Weidmann .......................... 340/677
4,267,554  5/1981  Loepfe et al. ......................... 66/163
4,491,831  1/1985  Sakai et al. ........................... 66/163

FOREIGN PATENT DOCUMENTS 1135384 11/1982 Canada .

Primary Examiner—Glen R. Swann, III
Attorney, Agent, or Firm—Bell, Seltzer, Park & Gibson

[57] ABSTRACT

The yarn tension at each of a plurality of yarn processing stations is continuously monitored, while continuously determining the mean value of the monitored tension at each station, and while also continuously determining the differential between the monitored value and the mean value. Also, an alarm signal is generated whenever the mean value leaves a predetermined tolerance range, and whenever the differential value leaves a second predetermined tolerance range. An alarm signal may serve to actuate a visual error indicator, or to shut down the associated processing station.

11 Claims, 4 Drawing Figures

4,720,702

METHOD AND APPARATUS FOR MONITORING THE TENSION OF AN ADVANCING YARN

BACKGROUND OF THE INVENTION

The present invention relates to a method and apparatus for centrally collecting measured values of a variable parameter from each of a plurality of monitored work stations. The method and apparatus find particular utility in a yarn textile processing machine which includes a plurality of yarn processing stations.

In German Pat. No. 30 05 746 and corresponding Canadian Pat. No. 1,135,384, there is disclosed a method wherein the data which is measured in a multi-position textile machine, and which continuously is received from a plurality of monitoring points, is collected and processed by a central data processing system. The ability to scan the monitored points is facilitated in that there are provided several decentralized data processing units positioned between the central data processing system and the monitoring points. Thus, only a limited number of monitoring points are respectively associated to each of the decentralized data processing units. These decentralized data processing units involve the scanning, and the intermediate storage of the data.

With the above described process, the scanning speed and scanning frequency are increased, but the system is relatively costly and the disadvantage remains that only the momentary values of the measurements are collected at the moment of scanning. In other words, only random values are determined and evaluated, and such random values are unable to provide a reliable indication of the operation of the process and the quality of the resulting product.

It is accordingly an object of the present invention to provide a method and apparatus for continuously monitoring a variable parameter at each of a plurality of work stations, and which more accurately reflects the operation of the process and the quality of the resulting product.

SUMMARY OF THE INVENTION

These and other objects and advantages of the present invention are achieved in the embodiments illustrated herein by the provision of a method and apparatus which involve continuously monitoring the value of the variable parameter at each of the work stations, while continuously determining the mean value of the monitored value of the parameter, and while continuously determining the differential between the monitored value and the mean value. Further, an alarm signal is generated whenever the mean value leaves a predetermined tolerance range, or whenever the differential value leaves a second predetermined tolerance range.

In a preferred embodiment, the method and apparatus involve the monitoring of the tension of an advancing yarn at each of a plurality of yarn processing stations of a yarn textile processing machine. Also, each of the tolerance ranges is identically predetermined for each of the yarn processing stations, which is preferably the same for all stations of the machine.

The method and apparatus of the present invention may be employed for example, in a false twist crimping machine to continuously measure the tension of each yarn being processed, and so as to collect and evaluate the monitored values so that it is possible to continually gather and monitor all critical operating conditions. In modern textile machines, this typically involves the processing of about 216 yarns. The alarm signals which are produced may be used to signal a critical operating condition at one processing position, or to shut down such position, for example by actuating a yarn cutter.

The alarm signals which are produced by the method of the present invention are preferably separately processed so as to actuate an optical or accoustical error indicator associated with the monitored position, or to sever the yarn which is being processed at the monitored position.

As indicated, the method and apparatus of the present invention may be conducted so as to continually monitor the yarn tension. The invention is based on the recognition that the yarn tension is an essential criterion for the quality of the yarn produced, particularly in the case of false twist texturing of man-made filament yarns, and that an uninterrupted monitoring of the yarn tension and particularly of the yarn tension peaks, is desirable. The present invention avoids the disadvantage that all fluctuations of the yarn tension are accordingly collected and centrally evaluated. To this end, each yarn tension sensor is so constructed and electrically connected that for quality control only two decisive signals are produced, namely, an alarm signal when the mean value deviates from its predetermined tolerance range, and an alarm signal when the difference between the measured signal and the mean value deviates from a second predetermined tolerance range. It has been found that the mean value and the deviation of the measured signal from the mean value provide an adequate statement as to quality of the yarn produced.

BRIEF DESCRIPTION OF THE DRAWINGS

Some of the objects and advantages having been stated, others will become apparent as the description proceeds, when taken in conjunction with the accompanying drawings, in which.

DETAILED DESCRIPTION OF THE PREFERRED EMBODIMENT

Figure 1:
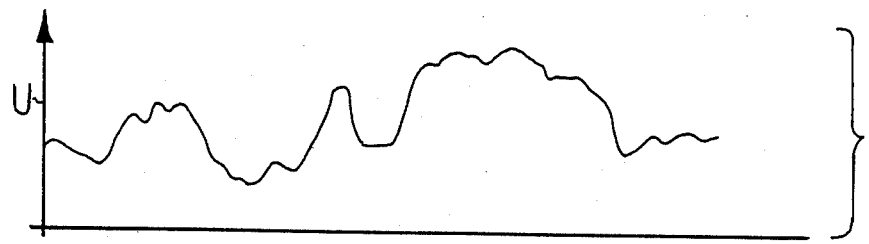
FIG. 1 is a diagram illustrating a segment of a graph of yarn tension versus time, with the yarn tension being indicated by an output signal U from a tension sensor.
Figure 2:
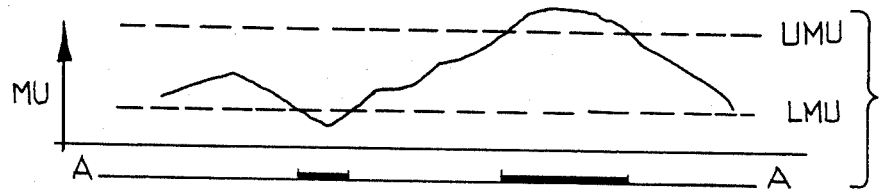
FIG. 2 is a similar diagram illustrating the mean value MU which results from the yarn tension shown in FIG. 1.
Figure 3:
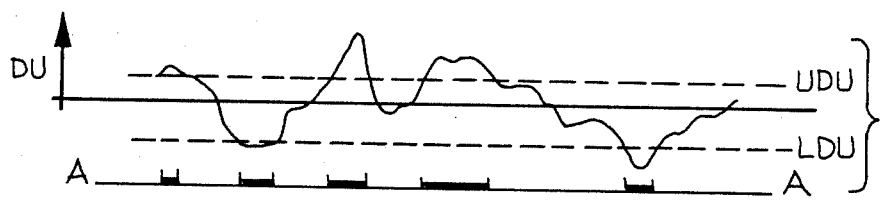
FIG. 3 is a diagram illustrating the differential value DU which is representative of the difference between the measured output signal U and the mean value MU.

Referring more particularly to the FIGS. 1-3, the mean (i.e. average) value is determined by supplying the output signal U (voltage) to an electrical filter having a relatively long time constant. The selection of the time constant permits the mean value to be influenced, and the greater the time constant which is selected, the less short term fluctuations of the output signal influence the mean value MU.

As a function of the mean value, an alarm signal A is generated, as shown in the bar diagram portion of FIG. 2, when the monitored mean value leaves a predetermined tolerance range between upper limiting value UMU and the lower limiting value LMU. The generation of the mean value also permits the determination of the long term level of the yarn tension.

As shown in FIG. 3, a differential signal DU is further produced from the measured signal U and the mean value MU. The differential signal indicates whether the yarn tension is maintained within a predetermined tolerance range about the mean value, or whether intolerable tension fluctuations occur. As shown in the diagram, gradually occurring changes of the yarn tension are only signalled when the tolerance range between UMU and LMU is exceeded. Short term fluctuations are picked up however, even though they do not influence the average value to a significant extent, via the generation of the differential signal DU, and they are signalled as an alarm signal A as shown in the bar diagram portion of FIG. 3, when the differential signal DU leaves a predetermined tolerance range between the upper limiting value UDU and the lower limiting value LDU.

It should be noted that the tolerance ranges for the mean value and for the differential value will be determined empirically, after having previously defined the desired yarn quality.

Figure 4:
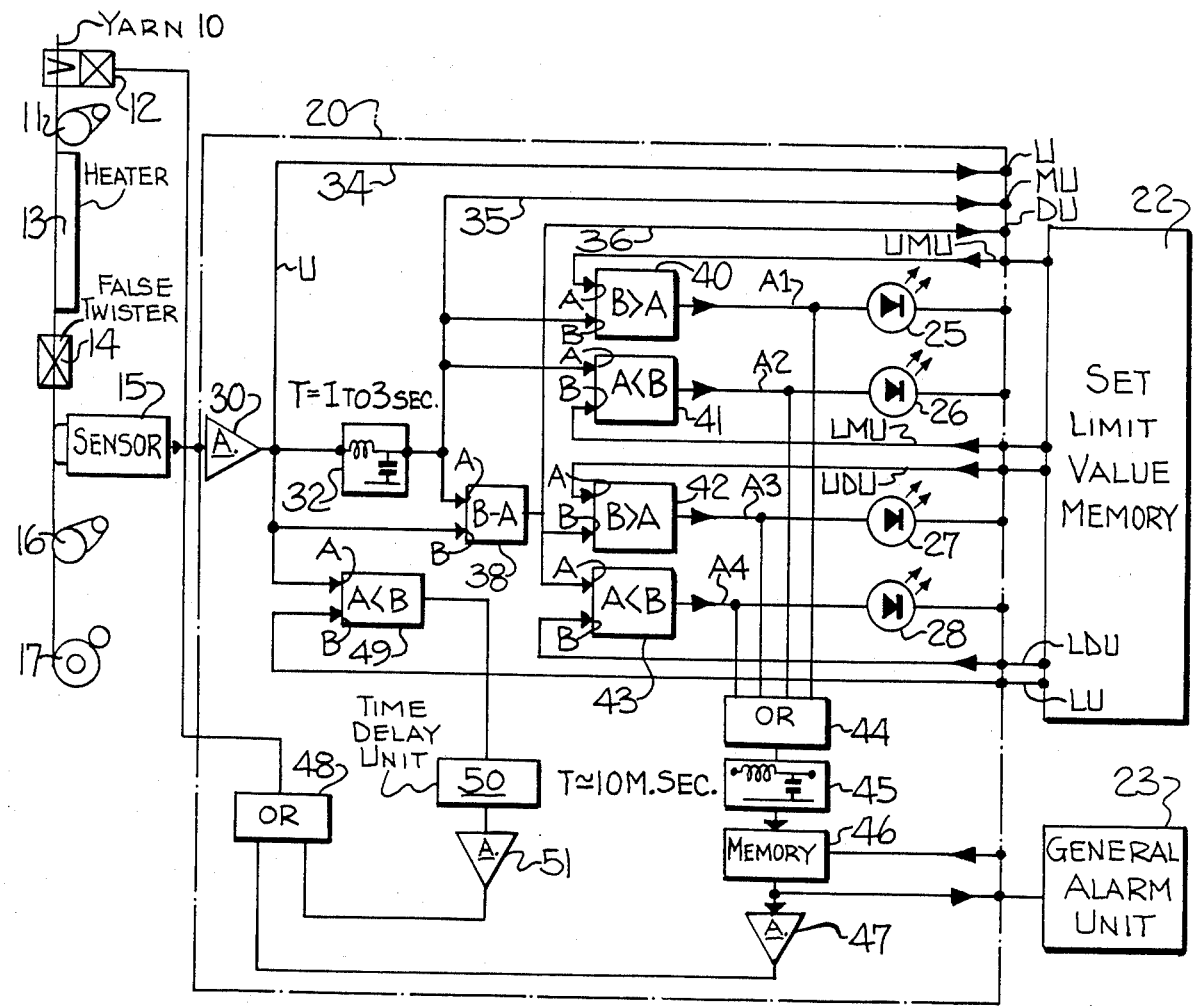
FIG. 4 is a schematic diagram illustrating an apparatus and electrical control circuit in accordance with the present invention.

FIG. 4 is a shematic diagram illustrating a yarn processing station and associated control circuitry in accordance with the present invention. The left hand portion of the diagram illustrates a yarn processing station, and wherein a yarn 10 is withdrawn from a supply roll or other source (not shown) by delivery roll 11. The yarn advances past a yarn cutter 12, and then it is guided across and in contact with a heater 13, through a false twister 14, and past a yarn sensor 15. The yarn is withdrawn from the false twisting zone by delivery roll 16 and wound onto a package 17 by means of a conventional winder.

The yarn cutter 12 may be of any conventional design, such as the cutter illustrated in Morrocco et al U.S. Pat. No. 3,526,348. The false twister 14 may be of the type as shown in Lorenz U.S. Pat. No. 3,813,868 or Dammann et al, U.S. Pat. No. 4,339,915. The yarn sensor 15 is also conventional, and may for example be of the type shown in copending Mink et al U.S. application Ser. No. 833,906, now U.S. Pat. No. 4,677,860. The yarn sensor 15 is designed to produce an output voltage signal U which varies in accordance with the yarn tension of the yarn 10 between false twister 14 and delivery roll 16.

The output signal U of the sensor 15 is transmitted to a circuit 20, which is illustrated within the dash-dot line in FIG. 4. Circuit 20 is associated with each position of a multi-position false twist machine, and with the yarn sensor 15 of such position. The circuit 20 receives predetermined tolerance values from a set limit value memory 22 which is described below in more detail. Memory 22 is associated with a group of stations of the multi-position texturing machine. Circuit 20 produces one output signal to the yarn cutter 12 and another output signal to a general alarm unit 23 which is also associated with a group of stations. Circuit 20, furthermore, produces output signals to alarm units 25, 26, 27, 28 which will be described below in more detail. These alarm units are correlated to the associated processing station.

The output signal of yarn sensor 15 is fed to amplifier 30 and then to filter 32. The filter is a circuit containing an induction coil and a capacitor, the circuit having a delay time constant of for example one to three seconds. The output signal of the amplifier 30 is a voltage U which may be fed to a central microprocessor for further processing and calculation via line 34. The output of filter 32 is the mean value MU which may also be fed to a general microprocessor via line 35 for further processing and calculation. On the other side, signal U and signal MU are fed to differential amplifier 38 producing an output signal DU which represents the difference of the input signals U and MU. The output signal DU of the differential amplifier 38 may be fed via line 36 to the central microprocessor for further processing and calculation.

The output signal MU of the filter 32 is furthermore used to produce alarm signals A1 and A2, if the mean value MU leaves the predetermined range of tolerance. The predetermined range of tolerance is defined by the upper limit of the mean value UMU and by the lower limit of the mean value LMU, both of which are stored in the limit value memory 22 and fed to circuit 20 via respective lines. The circuit 20 for this purpose contains triggers 40 and 41. Trigger 40 is fed by the mean value MU and the upper limit of the mean value UMU, and it is designed to produce an output signal A1, if the mean value exceeds the set upper limit of the mean value. Trigger 41 is designed to receive the mean value MU and the set lower limit of the mean value LMU as an input signal and to produce an output signal A2, if the mean value MU is lower than the set lower limit of the mean value.

The circuit 20 also produces alarm signals A3, A4, if the differential signal DU exceeds the predetermined range which is defined by a set upper limit of the differential value UDU and the set lower value of the differential value LDU. The predetermined upper and lower limits are stored in the limit value memory 22 and fed as input signals to triggers 42 and 43, respectively, of the circuit 20. The other input signal to the triggers 42 and 43 is the differential signal DU which is the output of differential amplifier 38 as described above. If the differential signal DU is greater than the set upper limit UDU, trigger 42 produces alarm signal A3. If differential value DU is smaller than the set lower limit LDU, trigger 43 produces alarm signal A4. Each of the alarm signals A1, A2, A3, A4 is fed to either one of the alarm units 25–28 which are associated with this position and which are, e.g., designed as a light emitting diode integrated into the circuit 20. Furthermore, alarm signals A1 to A4 are fed to OR gate 44, delay time unit 45, memory 46 and amplifier 47. The OR gate 44 produces an output signal, if any one of the alarm signals A1 to A4 is present. The delay time unit has a delay constant of about 10 msec, and is designed to prevent an output signal from a transient and irrelevant disturbance of the yarn texturing process, and which could result in the yarn 10 being cut by yarn cutter 12. The memory 46 ensures that a general alarm unit 23, which is associated with a group of stations or with the entire machine, will be able to generate a permanent signal to show that the production is disturbed and/or terminated.

The output signal of the memory 46 is also fed to an amplifier 47 and from there to OR gate 48, which receives another signal to be more fully described below. The output signal of the amplifier 47 produces an output signal of the OR gate 48, which in turn is fed to the yarn cutter 12 to cause cutting of the yarn and interruption of the texturizing or draw-texturizing process, as the case may be. The other input signal to OR gate 48 is produced by trigger 49 via delay time unit 50 and amplifier 51. Trigger 49 is fed by the value U representing the measured yarn tension and by a second set value LU stored in set limit value memory 22 and representing the lowest accepted value of the yarn tension. It should be noted that this value LU is preferably set at zero. Trigger 49 produces an output signal, if the measured value U is lower than or equal to the set value LU. The delay time constant of unit 50 may be about 10 msec. The output signal of trigger 49 is, as mentioned above, fed to OR gate 48 and causes yarn cutter 12 to cut the yarn upstream of delivery roll 11, if and when the yarn tension is below a set value or in case of a yarn break between delivery rolls 11 and 16.

In the drawings and specification, there has been set forth a preferred embodiment of the invention, and although specific terms are employed, they are used in a generic and descriptive sense only and not for purposes of limitation.

That which is claimed is:

1. A method of monitoring a variable parameter at a work station comprising the steps of
   continuously monitoring the value of the parameter, while continuously determining the mean value of the monitored parameter, and while also continuously determining the differential between the monitored value and the mean value, and
   generating an alarm signal whenever the mean value leaves a predetermined tolerance range, or whenever the differential value leaves a second predetermined tolerance range.

2. A method of monitoring the tension of an advancing yarn at each of a plurality of monitored yarn processing stations of a yarn processing machine and comprising the steps of
   continuously monitoring the value of the tension of the advancing yarn at each of the yarn processing stations, while continuously determining the mean value of the monitored tension of each of the yarns, and while also continuously determining the differential between the monitored value and the mean value for each of the yarns, and
   generating an alarm signal whenever the mean value for one of the advancing yarns leaves a predetermined tolerance range, or whenever the differential value for one of the advancing yarns leaves a second predetermined tolerance range.

3. The method as defined in claim 2 wherein the step of generating an alarm signal includes generating an alarm signal which is correlated to the associated yarn processing station upon the occurrence of either of said contingencies.

4. The method as defined in claim 2 wherein the step of generating an alarm signal includes severing the yarn being processed at the associated yarn processing station upon the occurrence of either of said contingencies.

5. The method as defined in claim 4 wherein the step of severing the yarn includes passing the alarm signal through a time delay circuit having a predetermined time constant so as to prevent the severing of the yarn in the event of the presence of a short and irrelevant alarm signal.

6. The method as defined in claim 5 wherein the step of severing the yarn includes generating a general alarm signal which is associated with a group of yarn processing stations of the machine to indicate that the yarn production at at least one of the associated stations has been terminated.

7. An apparatus for monitoring the tension of an advancing yarn at each of a plurality of monitored yarn processing stations of a yarn processing machine comprising
   sensor means for continuously monitoring the value of the tension of the advancing yarn at each of the yarn processing stations and for producing a continuous output signal representative of the value of the tension of each yarn,
   circuit means operatively connected to the sensor means for continuously determining the mean value of the monitored tension of each of the yarns, and for also continuously determining the differential between the monitored value and the mean value for each of the yarns, and
   means for generating an alarm signal whenever the mean value for one of the advancing yarns leaves a predetermined tolerance range, or whenever the differential value for one of the advancing yarns leaves a second predetermined tolerance range.

8. The apparatus as defined in claim 7 wherein said means for generating an alarm signal acts to generate an alarm signal whenever said mean value leaves its associated tolerance range and said differential value simultaneously leaves its associated tolerance range.

9. The apparatus as defined in claim 8 further comprising means for severing the yarn being processed at each of said processing stations, and control means for actuating said severing means at one of said stations whenever the mean value of the associated yarn leaves a predetermined tolerance range and whenever the differential value of the associated yarn leaves a second predetermined tolerance range.

10. The apparatus as defined in claim 9 wherein said control means includes time delay circuit means having a predetermined time constant so as to prevent the severing of a yarn in the event of a short and irrelevant departure from one of said tolerance ranges.

11. The apparatus as defined in claim 10 wherein said control means further includes means for generating a general alarm signal which is associated with a group of yarn processing positions of the machine to indicate that the yarn production at at least one of the associated positions has been terminated.

* * * * *